United States Patent
Platzek et al.

(10) Patent No.: US 6,894,151 B2
(45) Date of Patent: May 17, 2005

(54) LITHIUM COMPLEXES OF N-(1-HYDROXYMETHYL-2,3-DIHYDROXYPROPYL)-1,4,7-TRISCARBOXYMETHYL-1,4,7,10-TETRAAZACYCLODODECANE, THEIR PRODUCTION AND USE

(75) Inventors: Johannes Platzek, Berlin (DE); Peter Blaszkiewicz, Berlin (DE); Orlin Petrov, Berlin (DE); Holger Hoffmann, Menden (DE)

(73) Assignee: Shering Aktiengesellschaft, Berlin (DE)

( * ) Notice: Subject to any disclaimer, the term of this patent is extended or adjusted under 35 U.S.C. 154(b) by 198 days.

(21) Appl. No.: 10/013,840

(22) Filed: Dec. 13, 2001

(65) Prior Publication Data

US 2002/0128472 A1 Sep. 12, 2002

Related U.S. Application Data

(60) Provisional application No. 60/258,311, filed on Dec. 28, 2000.

(30) Foreign Application Priority Data

Dec. 15, 2000 (DE) .......................................... 100 64 467

(51) Int. Cl.$^7$ .......................... C07F 5/00; C07D 257/02

(52) U.S. Cl. ......................................... 534/16; 540/474
(58) Field of Search ............................ 534/16; 540/474

(56) References Cited

U.S. PATENT DOCUMENTS

| | | | |
|---|---|---|---|
| 5,980,864 A | 11/1999 | Platzek et al. | ........... 424/9.363 |
| 5,994,536 A | 11/1999 | Petrov et al. | ................ 540/474 |

FOREIGN PATENT DOCUMENTS

| | | |
|---|---|---|
| EP | 0 448 191 A | 9/1991 |
| WO | WO 98 55467 A | 12/1998 |

OTHER PUBLICATIONS

J. Platzek et al., "Synthesis and Structure of a New Macrocyclic Polyhydroxylated Gadolinium Chelate Used As Contrast Agent for Magnetic Resonance Imaging," Inorg. Chem., Bd. 36, Nr. 26, 1997, pp. 6086–6093, XP002199426.

Primary Examiner—Brenda Coleman
(74) Attorney, Agent, or Firm—Millen, White, Zelano & Branigan

(57) ABSTRACT

The invention relates to crystalline lithium complexes of N-(1-hydroxymethyl-2,3-dihydroxypropyl)-1,4,7-triscarboxymethyl-1,4,7,10 tetraazacyclododecane, their production and the recovery of the salt-free gadolinium complex of N-(1-hydroxymethyl-2,3-dihydroxypropyl)-1,4, 7-triscarboxymethyl-1,4,7,10 tetraazacyclododecane from the latter without the use of ion exchangers.

19 Claims, No Drawings

LITHIUM COMPLEXES OF N-(1-HYDROXYMETHYL-2,3-DIHYDROXYPROPYL)-1,4,7-TRISCARBOXYMETHYL-1,4,7,10-TETRAAZACYCLODODECANE, THEIR PRODUCTION AND USE

This application claims the benefit of the filing date of German Patent Application No. 10064467.8 filed Dec. 15, 2000 and U.S. Provisional Application No. 60/258,311 filed Dec. 28, 2000.

The invention relates to the subjects characterized in the claims, i.e., lithium complexes of N-(1-hydroxymethyl-2,3-dihydroxy-propyl)-1,4,7-triscarboxymethyl-1,4,7,10-tetraazacyclododecane, their production and use.

Because of their importance as imaging diagnostic agents, especially MRI diagnostic agents, the production of metal complexes, especially of the gadolinium complex, the N-(1-hydroxymethyl-2,3-dihydroxypropyl)-1,4,7-triscarboxymethyl-1,4,7,10-tetraazacyclododecane "GADOBUTROL" (DE 4009119), had been attempted in various ways. Despite progress achieved compared to the original process, there is also a need primarily for more non-polluting and more economical possibilities of synthesis to be performed on an industrial scale.

This object is achieved by this invention.

It was found that, surprisingly enough, the crystalline complexing agents of general formula I according to the

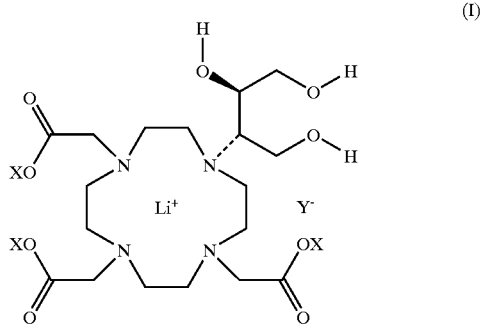

(I)

in which the three X altogether stand for n lithium ions and m hydrogen atoms, whereby n and m in each case mean the numbers 0 to 3, preferably 0.8–2.2, and the sum of n and m=3, and Y has the meaning of chloride and bromide, i.e., lithium complexes of N-(1-hydroxymethyl-2,3-dihydroxypropyl)-1,4,7-triscarboxymethyl-1,4,7,10-tetraazacyclododecane, are very well suited to produce the gadolinium complex GADOBUTROL in a way that is clearly superior to the closest prior art (Inorg. Chem. 1997, 36; 6086–6093 and DE 19724186.7).

Y preferably stands for chloride, and X stands for a lithium ion, and the remaining two stand for hydrogen atoms.

Starting from the N-(6-hydroxy-2,2-dimethyl-1,3-dioxepan-5-yl)-1,4,7,10-tetraazacyclododecane-LiCl complex or the LiBr complex (DE 19724 186.7), the compound according to the invention is produced with use of chloroacetic acid or bromoacetic acid, lithium hydroxide and hydrochloric acid or hydrobromic acid in water and crystallizes from an ethanol-water mixture. The crystalline complexing agent is complexed in water with gadolinium, and the complex is isolated salt-free by crystallization from ethanol/water without use of ion exchangers.

The advantages of this process are:

The complexing agent is isolated in crystalline form and in this case obtained in very pure form.

By the use of lithium hydroxide instead of sodium hydroxide (DE 197241867), the process for the production of the crystalline complexing agent avoids the expensive isolation of the apparatus-corrosive sodium chloride from the strongly acidic methanolic-aqueous solution. The lithium chloride or lithium bromide, which is produced in the process according to the invention instead of sodium chloride, remains in the weakly acidic ethanolic-aqueous mother liquor when the complexing agent crystallizes. The lithium can be recovered as lithium hydroxide from this mother liquor by treatment with an anion exchanger. The balance of the production process is significantly more advantageous with respect to the wastes.

The gadolinium can be metered accurately in complexing for the production of GADOBUTROL. As a result, the amount of production waste that contains gadolinium is reduced.

To remove salts and other by-products from the gadolinium complex, no ion exchanger is necessary in contrast to the process of the prior art. As a result, the operation of a corresponding technical unit and the associated waste products are no longer necessary.

The energy-intensive concentration by evaporation of the aqueous eluate of the ion exchanger is no longer necessary.

The compounds according to the invention are obtained by the LiCl or LiBr complex of N-(6-hydroxy-2,2-dimethyl-1,3-dioxepan-5-yl)-1,4,7,10-tetraazacyclododecane in polar solvents, such as water, primary and secondary alcohols, e.g., ethanol or isopropanol, DMF, dimethoxyethane, diethylene glycol dimethyl ether or mixtures of these solvents, preferably in water, with chloroacetic acid or bromoacetic acid, preferably with chloroacetic acid, and lithium hydroxide at temperatures of between 40 and 150° C., preferably at 40 to 90° C., a pH of between 8 and 14, preferably at a pH of 9 to 13, being reacted within 0.5 hour to 24 hours, preferably 1 to 6 hours.

To isolate the product, it is set at pH 3.5 to 4.5, preferably at pH 3.8 to 4.2, with hydrochloric acid, hydrobromic acid, acetic acid, trifluoroacetic acid or p-toluenesulfonic acid, preferably with hydrochloric acid, and crystallized from a mixture of water and ethanol.

To convert the complexing agent of general formula I into the gadolinium complex of general formula II, the complexing agent is dissolved in water, set at a pH of about 3.6 by adding hydrochloric acid, the calculated amount of gadolinium oxide is added, complexed at 50 to 100° C., preferably at 70 to 100° C., and the gadolinium complex is crystallized by adding ethanol.

The invention is explained by the examples below:

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure[s] of all applications, patents and publications, cited above, and of corresponding German application No. 10064467.8, filed Dec. 15, 2000, and U.S. Provisional Application No. 60/258,311, filed Dec. 28, 2000, are hereby incorporated by reference.

EXAMPLE 1

The production of the lithium complex of (N-(1-hydroxymethyl-2,3-dihydroxypropyl)-1,4,7-triscarboxymethyl-1,4,7,10-tetraazacyclododecane 38.5 g of chloroacetic acid is introduced, dissolved in 40 g of water, and the solution is cooled to 0 to 10° C. 17.1 g of lithium hydroxide monohydrate is added to this solution. This solution is added to a solution of 41.25 g (114.95 mmol) of the lithium chloride complex of N-(6-hydroxy-2,2-dimethyl-1,3-dioxepan-5-yl)-1,4,7,10-tetraazacyclododecane, dissolved in about 45 ml of water. The mixture is heated to about 65°, and a total of 14.6 g of lithium hydroxide monohydrate is added at this temperature within 2 hours in portions. Then, it is stirred for 1 more hour at 65° C. The solution is then acidified with hydrochloric acid to pH 4. 500 ml of ethanol is added to the solution during the course of 75 minutes at an internal temperature of 65 to 75° C. The crystallization of the lithium complex starts spontaneously from the end of the addition of ethanol. After the addition of ethanol is completed, it is refluxed for 2 hours, then it is cooled to room temperature, the crystallizate is filtered off, washed with 2×20 ml of 80% ethanol and 2×20 ml of 90% ethanol, and it is dried at 50° C.

Yield: 51.6 g=93.67 mmol taking into consideration the water content=81.5% of theory.

Analysis:

H-NMR in $D_2O$: Multiplet between 3.0 and 3.9 ppm for N—$CH_2$—$CH_2$—N (4×), N—$CH_2$—COOH (3×), N—CH 1×), CH—OH (1×) and $CH_2$—OH (2×).

IR (KBr, $cm^{-1}$): 3440, 3360, 3300, 1675, 1650, 1590, 1400

FAB-MS (Matrix NBA-glycerol-DMSO: 451 (M+H), 45 (M+Li), 473 (M+Na)

FAB-MS (Matrix Magic Bullet) 451 (M+H), 457 (M+7)

Water content 9.45%, ethanol content 0.0%.

Elementary analysis calculated for the mixture: Li complex+9.45%=2.89 mol of water:

| % | C | H | Cl | Li | N | Water | EtOH |
|---|---|---|---|---|---|---|---|
| Theory: | 39.25 | 7.1 | 6.44 | 2.52 | 10.17 | 9.45 | 0 |
| Found | 38.82 | 6.86 | 6.83 | 2.64 | 10.17 | 9.45 | 0 |
| Difference | −0.43 | −0.24 | 0.39 | 0.12 | 0 | 0 | 0 |

EXAMPLE 2

The production of the gadolinium complex of (N-(1-hydroxymethyl-2,3-dihydroxypropyl)-1,4,7-triscarboxymethyl-1,4,7,10-tetraazacyclododecane (GADOBUTROL)

51.6 g (93.67 mmol taking into consideration 9.45% water) of crystalline lithium complex of N-(1-hydroxymethyl-2,3-dihydroxypropyl)-1,4,7-triscarboxymethyl-1,4,7,10-tetraazacyclododecane (Example 1) is dissolved in 51 g of completely demineralized water, and the solution is set at a pH of 3.5 with concentrated hydrochloric acid. 16.9 g of $Gd_2O_3$ is added to the solution, and the suspension is stirred for 1 hour at 90° C. The suspension is turned into a solution. The pH of this solution is optionally set at 7 with solid lithium hydroxide monohydrate. At a temperature of about 78° C., the solution is gradually mixed with 960 ml of ethanol during the course of 2 hours. A suspension is produced. The latter is refluxed for 5 hours after the addition of ethanol is completed. The suspension is then cooled to room temperature, the crystallizate is filtered off, washed with 100 ml of ethanol and dried at 50° C.

Yield: 51.02 g=80.3 mmol taking into consideration the water content=85.73% of theory.

Drying loss 1.06%, water content 4.74%.

Analysis for GADOBUTROL with 1.7 mol of water= 4.82% and 0.53 mol of LiCl:

| % | C | H | N | Cl | Li | Gd | Water | EtOH |
|---|---|---|---|---|---|---|---|---|
| Theory: | 32.87 | 5.27 | 8.52 | 2.86 | 0.56 | 23.91 | 4.82 | 0 |
| Found | 32.96 | 5.25 | 8.49 | 2.91 | 0.53 | 23.85 | 4.74 | 0 |
| Difference | 0.09 | −0.02 | −0.03 | 0.05 | −0.03 | −0.06 | −0.08 | 0 |

Recrystallization for Complete Demineralization 51.02 g of GADOBUTROL, crude=80.3 mmol taking into consideration the water content, is dissolved in 47 ml of water at about 75° C., and 470 ml of ethanol is gradually added to the solution during the course of one hour. A suspension is produced. After the addition of ethanol is completed, the latter is refluxed for 2 hours, then it is cooled to 20° C., stirred for 1 hour at this temperature, the crystallizate is suctioned off, washed with 66 ml of ethanol and dried at 50° C.

Yield: 47.08 g=74.84 mmol taking into consideration the water content=93.2% of theory Analysis: Water content 3.92%, ethanol content 0.16%, elementary analysis for: GADOBUTROL with 1.35 mol of water=3.86%, 0.02 mol of EtOH=0.15% and 0 mol of LiCl:

| % | C | H | N | Cl | Li | Gd | Water | EtOH |
|---|---|---|---|---|---|---|---|---|
| Theory: | 34.4 | 5.4 | 8.89 | 0 | 0 | 24.96 | 3.86 | 0.15 |
| Found | 34.48 | 5.01 | 8.76 | 0 | <0.01 | 24.96 | 3.92 | 0.16 |
| Difference | 0.08 | −0.39 | −0.13 | 0 | <0.01 | 0.09 | 0.06 | 0.01 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula I

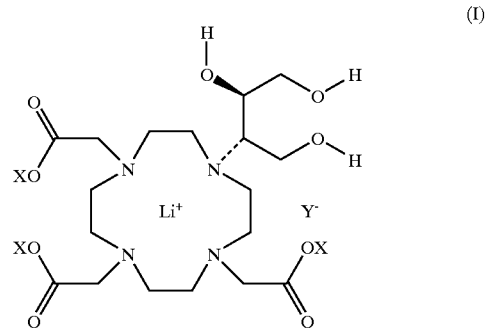

in which the three X's altogether, independently, stand for n lithium ions and m hydrogen atoms, whereby n and m in each case, independently, mean the numbers 0 to 3, and the sum of n and m=3, and Y has the meaning of chloride or bromide.

2. A process for production of a compound of formula I according to claim 1, comprising reacting N-(6-hydroxy-2,2-dimethyl-1,3-dioxepan-5-yl)-1,4,7,10-tetraazacyclododecane or its complex with lithium chloride or lithium bromide with chloroacetic acid or bromoacetic acid and lithium hydroxide in polar solvent at a temperature of 40–150° C. and a pH of 8–14.

3. A method of producing a compound of formula II

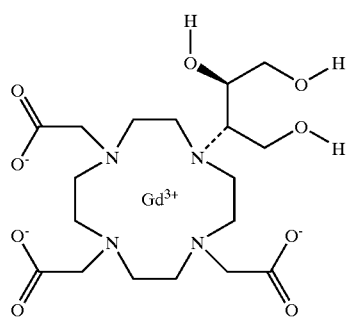

(II)

comprising complexing a compound of formula I according to claim 1.

4. A compound of formula I according to claim 1, wherein Y stands for chloride, and one X stands for a lithium ion, and the two remaining X's stand for hydrogen atoms.

5. A compound of formula I according to claim 1, wherein n and m in each case independently mean the numbers 0.8–2.2.

6. A compound of formula I according to claim 1, wherein the compound is in crystalline form.

7. A process according to claim 2, further comprising crystallizing a compound of formula I according to claim 1 from an ethanol-water mixture.

8. A method according to claim 3, further comprising isolating salt-free a compound of formula II from ethanol/water without using an ion exchanger.

9. A process according to claim 2, further comprising recovering lithium hydroxide by treatment with an anion exchanger.

10. A process according to claim 2, wherein the polar solvent is water, a primary alcohol, a secondary alcohol, DMF, dimethoxy-ethane, diethylene glycol dimethyl ether, or a mixture thereof.

11. A process according to claim 2, wherein the polar solvent is ethanol or isopropanol.

12. A process according to claim 2, wherein the reaction is at a temperature of 40°–90° C.

13. A process according to claim 2, wherein the pH is within the range of 9–13.

14. A process according to claim 2, wherein the reaction is carried out for 0.5–24 hours.

15. A process according to claim 2, wherein the reaction is carried out for 1–6 hours.

16. A process according to claim 2, further comprising isolating the compound of formula I by setting the pH within the range of 3.5–4.5 with hydrochloric acid, hydrobromic acid, acetic acid, trifluoroacetic acid, or p-toluene sulfonic acid.

17. A process according to claim 2, further comprising isolating the compound by setting the pH within the range of 3.8–4.2.

18. A process according to claim 17, wherein the pH is set with hydrochloric acid.

19. A method according to claim 3, further comprising dissolving a compound of formula I in water, setting a pH of about 3.6 by adding hydrochloric acid, adding a calculated amount of gadolinium oxide, complexing at 50–100° C., and crystallizing the compound of formula II by adding ethanol.

* * * * *